US012799072B2

(12) United States Patent
Kramer et al.

(10) Patent No.: US 12,799,072 B2
(45) Date of Patent: Nov. 17, 2026

(54) CREATINE CARBONATE AND METHODS OF PRODUCTION AND USES

(71) Applicant: ThermoLife International, LLC, Signal Hill, CA (US)

(72) Inventors: Ronald Kramer, Signal Hill, CA (US); Alexandros Nikolaidis, Nea Kallikratia (GR)

(73) Assignee: ThermoLife International, LLC, Signal Hill, CA (US)

( * ) Notice: Subject to any disclaimer, the term of this patent is extended or adjusted under 35 U.S.C. 154(b) by 305 days.

(21) Appl. No.: 18/765,163

(22) Filed: Jul. 5, 2024

(65) Prior Publication Data

US 2025/0019344 A1 Jan. 16, 2025

Related U.S. Application Data

(60) Provisional application No. 63/525,087, filed on Jul. 5, 2023.

(51) Int. Cl.

*C07C 279/14* (2006.01)
*A61K 9/46* (2006.01)
*A61K 31/195* (2006.01)

(52) U.S. Cl.

CPC .......... *C07C 279/14* (2013.01); *A61K 9/0007* (2013.01); *A61K 31/195* (2013.01)

(58) Field of Classification Search

CPC .. A61K 31/195; A61K 31/198; A61K 9/0007; C07C 279/14; A23L 33/10

See application file for complete search history.

(56) References Cited

U.S. PATENT DOCUMENTS

| | | | |
|---|---|---|---|
| 7,301,051 | B2 | 11/2007 | Boldt |
| 2011/0034421 | A1 | 2/2011 | Miller |

FOREIGN PATENT DOCUMENTS

| | | |
|---|---|---|
| CN | 101331949 | 12/2008 |
| WO | 2018157258 | 9/2018 |

OTHER PUBLICATIONS

Barber, J. J. et al., "Effects of combined creatine and sodium bicarbonate supplementation on repeated sprint performance in trained men", Journal of strength and conditioning research, 2013, vol. 27, No. 1, pp. 252-258.

*Primary Examiner* — Umamaheswari Ramachandran

(74) *Attorney, Agent, or Firm* — Pacer K. Udall; Booth Udall, PLC

(57) ABSTRACT

Creatine carbonate is disclosed along with its methods of production and certain uses. Also disclosed are compositions comprising creatine carbonate, for example a dietary supplement or a pharmaceutical composition.

39 Claims, 2 Drawing Sheets

CREATINE CARBONATE AND METHODS OF PRODUCTION AND USES

CROSS-REFERENCE TO RELATED APPLICATIONS

This application claims priority to and the benefit of U.S. provisional patent application 63/525,087, filed Jul. 5, 2023 titled "Creatine Carbonate and Methods of Production and Uses," the entirety of the disclosure of which is hereby incorporated by this reference.

FIELD OF THE INVENTION

The disclosure relates to creatine carbonate and its methods of production and uses.

BACKGROUND OF THE INVENTION

Creatine is a nonessential amino acid and is also a nitrogenous organic acid. Creatine is independently manufactured by the human body and does not need to be obtained directly through dietary intake. Creatine plays a significant role in providing muscles with energy.

Creatine is presently used in the dietary supplement industry to supplement creatine production in the body. Creatine is also presently used in the dietary supplement industry to increase muscle-mass gains, improve athletic performance and strength. Creatine has also been utilized in the management of many diseases associated with limited energy production and creatine concentration in the body.

However, creatine supplementation is often accompanied by side effects such as diarrhea and stomach upset, pain, and cramps. These side effects are more pronounced with doses of creatine supplementation higher than the typical maintenance dose (5 grams creatine monohydrate) (Ostojic et al., "Gastrointestinal Distress After Creatine Supplementation in Athletes: Are Side Effects Dose Dependent?," *Res Sports Med.* 2008, 16 (1): 15-22). In the market of creatine supplementation, the vast majority of consumers are looking to "load" with creatine (i.e. achieve saturation of their muscles with creatine), which commonly involves a single dose of up to 20 grams creatine. Thus, alternate forms of creatine for those desiring to "load" with creatine are needed to minimize the onset of gastrointestinal side effects.

Another big problem associated with creatine supplementation and administration is creatine's poor solubility in water and acidic pH, such as that of the stomach. One approach to solve this problem has been forming salts with acids, such as creatine hydrochloride and creatine citrate. However, the acidic solution formed by the dissolution of such salts can be damaging to tooth enamel. Furthermore, the acid salts decrease the stability of creatine in solution, as most acids tend to promote creatine cyclization to creatinine. Such salts also may have objectionable taste.

Another obstacle with creatine supplementation with creatine salts is that some of these acidic salt forms may be less soluble or dissolve at a slower rate than regular creatine in strong acidic environments such as that of the stomach. Also, as carbonated drinks are increasing in popularity, these acidic salt forms lack the ability to readily form carbonated drinks in reaction with an acid, which is the common way of preparing such drinks. Thus, carbonate salts from creatine would be preferred for preparing carbonated creatine drinks. However, regular methods of producing carbonate salts (i.e. dissolving said compound in carbonated water, evaporating the solution and collecting the carbonate) do not work with creatine.

SUMMARY OF THE INVENTION

Creatine carbonate is disclosed. The compound has the structural formula of:

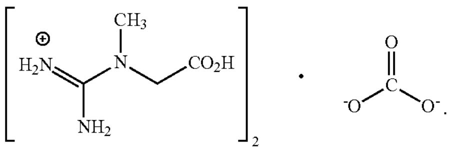

An effervescent formulation comprising creatine carbonate and an acid is also disclosed. In some aspects, the effervescent formulation does not comprise any other carbonate salt or bicarbonate salt other than the creatine carbonate.

A dietary supplement comprising a therapeutically effective dose of creatine carbonate is also described. In some aspects, the amount of creatine carbonate in a dose of the dietary supplement is about 1 mg to about 30,000 mg, about 2 mg to about 30,000 mg, about 1 mg to about 20,000 mg, about 2 mg to about 20,000 mg, about 1,000 mg to about 30,000 mg, about 2,000 mg to about 20,000 mg, about 5,000 mg to about 30,000 mg, or about 5,000 mg to about 20,000 mg. The dietary supplement may be in the form of a capsule, a cachet, a pill, a tablet, a powder, a granule, a pellet, a bead, a particle, a troche, a lozenge, a pastille, a solution, an elixir, a syrup, a tincture, a suspension, an emulsion, a mouthwash, a spray, a drop, an ointment, a cream, a gel, a paste, a transdermal patch, a suppository, a pessary, cream, a gel, a paste, a foam, or combinations thereof. In some embodiments, the dietary supplement is in an effervescent formulation.

In some implementations, the dietary supplement additionally comprises one or more of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and an acceptable carrier. In some aspects, the acceptable carrier comprises an excipient, a lubricant, a binder, a disintegrator, a diluent, an extender, a solvent, a suspending agent, a dissolution aid, an isotonic agent, a buffering agent, a soothing agent, an amphipathic lipid delivery system, or combinations thereof.

A pharmaceutical composition comprising a therapeutically effective dose of creatine carbonate is additionally described. The pharmaceutical composition provides a daily dosage of creatine carbonate of 1 to 30,000 mg of creatine in one or multiple unit dosage forms. In some embodiments, the pharmaceutical composition comprises creatine carbonate in a range of about 2 mg to about 30,000 mg, about 1 mg to about 20,000 mg, about 2 mg to about 20,000 mg, about 1,000 mg to about 30,000 mg, about 2,000 mg to about 20,000 mg, about 5,000 mg to about 30,000 mg, or about 5,000 mg to about 20,000 mg. In some aspects, the unit dosage form is a capsule, a cachet, a pill, a tablet, a powder, a granule, a pellet, a bead, a particle, a troche, a lozenge, a pastille, a solution, an elixir, a syrup, a tincture, a suspension, an emulsion, a mouthwash, a spray, a drop, an ointment, a cream, a gel, a paste, a transdermal patch, a suppository, a pessary, cream, a gel, a paste, a foam, or combinations thereof.

In some aspects, the pharmaceutical composition additionally comprises one or more of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and an acceptable carrier. In some implementations, the acceptable carrier comprises an excipient, a lubricant, a binder, a disintegrator, a diluent, an extender, a solvent, a suspending agent, a dissolution aid, an isotonic agent, a buffering agent, a soothing agent, an amphipathic lipid delivery system, or combinations thereof.

A method of synthesizing creatine carbonate is also described. The method comprises reacting a creatine salt with a carbonate salt. The creatine salt may be creatine hydrochloride. The carbonate salt may be ammonium carbonate. In particular implementations, creatine hydrochloride is contacted with ammonium carbonate. In some implementations, the method comprises dissolving ammonium carbonate in water and adding creatine hydrochloride, wherein the molar ratio of ammonium carbonate to creatine hydrochloride is about 2:1. In some aspects, the method further comprises collecting a formed precipitate by filtration. The method may further comprise drying the precipitate.

In other implementations, the creatine salt and carbonate salt may be combined at a molar ratio of 1:1 creatine to carbonate, especially in the presence of other cations beside creatine.

Methods of using creatine carbonate are also described. In some aspects, the method comprises administering a creatine carbonate salt to a subject wherein a daily dosage of creatine carbonate of 1 to 30,000 mg in one or multiple doses is administered to the patient. In some aspects, the daily dosage is administered in one dose. In other aspects, the daily dosage is administered in two to four doses. The route of administration is selected from topical, transdermal, oral, rectal, ophthalmic, nasal, vaginal, or parenteral routes. In particular implementations, creatine carbonate is administered orally. In some aspects, creatine carbonate is administered as a dietary supplement or as a pharmaceutical composition.

In some implementations, the dose of creatine carbonate is in the form of a capsule, a cachet, a pill, a tablet, a powder, a granule, a pellet, a bead, a particle, a troche, a lozenge, a pastille, a solution, an elixir, a syrup, a tincture, a suspension, an emulsion, a mouthwash, a spray, a drop, an ointment, a cream, a gel, a paste, a transdermal patch, a suppository, a pessary, cream, a gel, a paste, a foam, or combinations thereof. In some aspects, the dose of creatine carbonate additionally comprises one or more of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and an acceptable carrier. In some implementations, the acceptable carrier comprises an excipient, a lubricant, a binder, a disintegrator, a diluent, an extender, a solvent, a suspending agent, a dissolution aid, an isotonic agent, a buffering agent, a soothing agent, an amphipathic lipid delivery system, or combinations thereof.

In some implementations, creatine carbonate is administered to a subject to treat a creatine carbonate improvable condition, for example, cerebral creatine deficiency syndrome, sarcopenia, amyotrophic lateral sclerosis (ALS), Huntington disease, osteopenia, age-related cognitive decline, aging skin, chronic kidney disease (CKD), chronic obstructive pulmonary disease (COPD), cognitive function, congestive heart failure (CHF), depression, diabetes, fatigue, fibromyalgia, gyrate atrophy, hereditary motor and sensory neuropathy, HIV/AIDS-related wasting, hyperhomocysteinemia, inflammatory myopathies, juvenile idiopathic arthritis (JIA), McArdle disease, mitochondrial myopathies, multiple sclerosis (MS), muscle breakdown, muscle cramps, muscular dystrophy, neonatal apnea, osteoarthritis, Parkinson disease, peripheral arterial disease (PAD), post-operative recovery, Rett syndrome, rheumatoid arthritis (RA), schizophrenia, spinal cord injury, spinal muscular atrophy, and traumatic brain injury (TBI).

In some implementations, the subject is administered creatine carbonate topically, transdermally, orally, rectally, ophthalmically, nasally, vaginally, or parenterally. In some aspects of the subject being administered creatine carbonate orally, the subject is administered the creatine carbonate in an effervescent formulation comprising the creatine carbonate and an acid. In some embodiments, the effervescent composition further comprises a second carbonate salt or bicarbonate salt, wherein the second carbonate salt or bicarbonate salt is not the creatine carbonate.

A method of decreasing lactate production from physical activity is also disclosed. The method comprising administering to a subject prior to the subject performing the physical activity an effective amount of creatine carbonate. In some implementations, the subject is orally administered the creatine carbonate 5 to 120 minutes before the subject performs the physical activity.

BRIEF DESCRIPTION OF THE DRAWINGS

Implementations will hereinafter be described in conjunction with the appended and/or included DRAWINGS, where like designations denote like elements.

DETAILED DESCRIPTION OF THE INVENTION

Detailed aspects and applications of the disclosure are further described below, in any drawings/structures, and in the claims. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant art, that the present disclosure may be practiced without these specific details. It should be noted that there are many different and alternative configurations, devices, methods, and technologies to which the divulged disclosures may be applied. The full scope of the disclosures is not limited to the examples that are described below.

The singular forms “a,” “an,” and “the” include plural referents unless the context clearly dictates otherwise. Thus, for example, reference to “a step” includes reference to one or more of such steps.

It will be understood that the term “creatine carbonate” refers to the molecule of creatine carbonate depicted below, which is solid in regular room temperature:

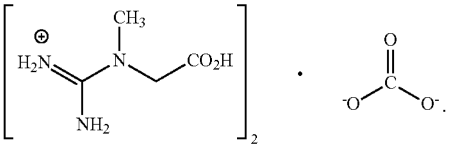

Figure 1:
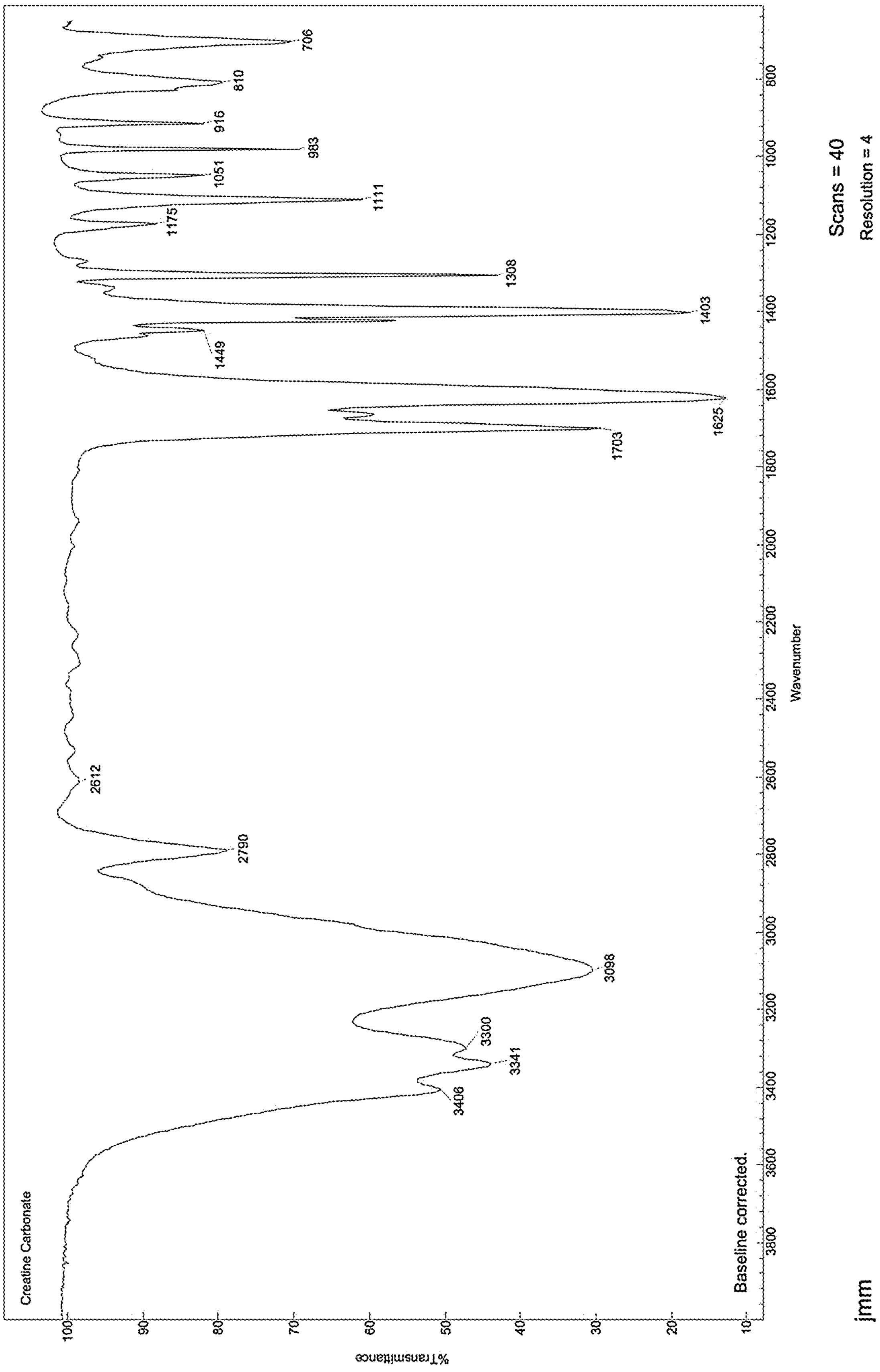
FIG. 1 is a spectra of creatine carbonate using FTIR.

The FTIR spectra of the compound is depicted in FIG. 1.

It will be understood that the term “creatine carbonate hydrate” refers to possible hydrates of creatine carbonate that can be formed after exposure of creatine carbonate to atmospheric humidity or after reaction of creatine carbonate with water to form creatine carbonate hydrate crystals. The hydrates formed can be a monohydrate, a dihydrate, a quasi-hydrate and the like.

As used herein, the term “effective amount” or “therapeutically effective amount” of a compound is that amount of compound which is sufficient to accomplish a specified task or function desired of the compound, for example, to provide a beneficial effect to the subject to which the compound is administered.

As used in herein, the term “pharmaceutically acceptable” is used in its broadest sense and may describe the quality of meeting Food and Drug Administration (FDA) standards, United States Pharmacopeial Standards (USP), US Department of Agriculture (USDA) standards for food-grade materials, commonly accepted standards of the nutritional supplement industry, industry standards, or botanical standards. These standards may delineate acceptable ranges of aspects of ingredients of a pharmaceutical composition such as edibility, toxicity, pharmacological effect, or any other aspect of a chemical, composition, or preparation used in implementations of a pharmaceutical composition.

As used herein, “pharmaceutically acceptable additive” or “additive” are terms used in their broadest sense. Particular implementations of the compositions described in this document may also comprise an additive (e.g. one of a solubilizer, an enzyme inhibiting agent, an anticoagulant, an antifoaming agent, an antioxidant, a coloring agent, a coolant, a cryoprotectant, dilutant, a hydrogen bonding agent, a flavoring agent, a flow agent, a plasticizer, a preservative, a sweetener, a thickener, and combinations thereof) and/or a carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof). These additives may be solids or liquids, and the type of additive may be generally chosen based on the type of administration being used. Those of ordinary skill in the art will be able to readily select suitable pharmaceutically acceptable additives from the disclosure in this document. In particular implementations, pharmaceutically acceptable additives may include, by non-limiting example, calcium phosphate, cellulose, stearic acid, crosscarmelose cellulose, magnesium stearate, and silicon dioxide.

As used in this document, “pharmaceutically effective” is a phrase used in its broadest sense, including, by non-limiting example, effective in a clinical trial or for a specific patient. When used in a method claim, pharmaceutically effective will mean in a dose enough to achieve the claim’s preamble. In some aspects, the effect to which the term “pharmaceutically effective” relates includes non-therapeutic uses, such as increase in athletic performance.

“About” as used herein when referring to a measurable value such as an amount, a temporal duration, and the like, is meant to encompass variations of +20%, +10%, +5%, +1%, and =0.1% from the specified value, as such variations are appropriate. It is to be understood that in the present specification, the use of the term “about” in connection with a numerical value also affords support for the exact numerical value as though it had been recited without the term “about”.

As used herein, the term “subject” refers to an animal. In some aspects, the subject is a mammal, for example a human.

As used herein, the term “disease” refers to a state of health of an animal (including humans) wherein the animal cannot maintain homeostasis, and not ameliorating physiological imbalance results in deterioration of the animal’s health.

In contrast, as used herein, the term “disorder” refers to a state of health in an animal in which the animal (including humans) is able to maintain homeostasis, but the animal’s state of health is less favorable than it would be in the absence of the disorder. Leaving the disorder untreated does not necessarily cause a further decrease in the animal’s state of health. However, in some aspects, leaving the disorder untreated can result in the animal developing a disease.

As used herein, a disease or disorder is “alleviated” if the severity of a symptom of the disease or disorder, the frequency with which such a symptom is experienced by a patient, or both, is reduced.

As used herein, a disease is “cured” if the disease no longer shows any symptoms and appropriate diagnostic tests show absence of the disease on a patient.

As used herein, the terms “treat,” “treatment,” and “treating,” a disease or disorder means reducing the severity and/or frequency, with which a sign and/or symptom of the disease or disorder is experienced by a subject. The subject may be symptomatic or asymptomatic at the time of treatment. In other words, “treat,” “treatment,” and “treating,” can be to reduce, ameliorate or eliminate signs or symptoms associated with a condition present in a subject, or can be metaphylactic or prophylactic, (i.e. to prevent or reduce the occurrence of the symptoms in a subject, or to delay onset of possible or expected signs or symptoms in a subject). Such prophylactic or metaphylactic treatment can also be referred to as prevention of the condition.

Disclosed herein is the carbonate salt of creatine. Surprisingly, up to 20 grams creatine carbonate could be orally administered to subjects without onset of gastrointestinal distress. Creatine carbonate does not exist in nature and cannot be isolated from natural sources. Thus, the disclosure also relates to making a creatine carbonate salt. The disclosed method cost effectively synthesizes creatine carbonate. The method comprises adding creatine hydrochloride to a saturated ammonium carbonate solution. Creatine carbonate then forms and precipitates, which can then be easily filtered out and isolated. Alternative implementations comprise forming first a solution of creatine hydrochloride by dissolving creatine hydrochloride in water or combining, in some implementations, about equimolar amounts of hydrochloric acid and creatine in water to produce a solution comprising creatine. The method then comprises adding ammonium carbonate or a solution of ammonium carbonate to the solution comprising creatine.

In the following description, and for the purposes of explanation, numerous specific details are set forth in order to provide a thorough understanding of the various aspects of the disclosure. It will be understood, however, by those skilled in the relevant art, that the present disclosure may be practiced without these specific details. It should be noted that there are many different and alternative configurations, devices, systems, methods, and technologies to which the divulged disclosures may be applied. The full scope of the disclosures is not limited to the examples that are described below.

In some implementations, the method comprises dissolving a carbonate salt in water to produce a solution and adding a creatine salt to the solution. The molar ratio of carbonate salt to creatine salt in the solution is about 2:1. In other implementations, the creatine salt and carbonate salt may be combined at a molar ratio of 1:1 creatine to carbonate, especially in the presence of other cations beside creatine.

The addition of the creatine salt to the solution produces a precipitate, which comprises creatine carbonate. Thus in some aspects, the method of synthesizing a creatine carbonate salt further comprises collecting the precipitate by filtration. The method may further comprise drying the precipitate. It is contemplated that other salts of creatine with acids stronger than carbonic acid could be used as a starting creatine salt material or to create an acidic solution of creatine that reacts with ammonium carbonate, including but not limited to: nitric acid, phosphoric acid, sulphuric acid, ascorbic acid, citric acid, fumaric acid, malonic acid, maleonic acid, adipic acid, pyruvic acid, nitrous acid, perchloric acid, oxalic acid, formic acid, cyanic acid, arsenic acid, permaganic acid, hydrosulfuric acid, acetic acid, bromic acid, iodic acid, chromic acid, bromic acid, thiocyanic acid, tartaric acid, phtalic acid, lactic acid, butyric acid, propionic acid, gallic acid, and salicylic acid.

It will also be understood that ammonium carbonate may be substituted for a salt of carbonic acid with a weak base. Examples include ethylamine carbonate, methylamine carbonate, guanidine carbonate and the like. Ammonium carbonate is preferred due to cost, availability (approved as a food additive) and relative ease to remove any residual ammonia with evaporation.

It will be understood that the creatine carbonate produced by this method does not need to be 100% pure creatine carbonate. Impurities, such as unreacted creatine, water, solvents and the reactants might exist at amounts deemed to be appropriate for the standards for which the creatine carbonate was prepared.

The disclosure also relates to compositions comprising creatine carbonate. In some aspects, creatine carbonate is combined with a dietary ingredient, a food additive, or a pharmaceutically acceptable additive to produce a dietary supplement or a pharmaceutical composition. In certain implementations, the composition is an effervescent formulation further comprising an acid. In some aspects, the effervescent formulation does not comprise any other carbonate salt or bicarbonate salt other than the creatine carbonate.

The described composition may be administered to a subject to increase physical/athletic performance, increase recovery from physical work and exercise, or treat a condition that negatively affects physical performance and recovery. In some aspects, the condition that negatively affects physical performance and recovery is the production of lactic acid from physical activity (for example, physical exercise or work). Thus, a method of decreasing lactate production from physical activity is disclosed. In some aspects, the reduction of lactate production can be achieved without ingestion of any other creatine supplements for up to 30 days before the physical activity. In other words, administration of creatine carbonate 5-120 minutes before physical activity is sufficient to decrease lactate production from the physical activity without creatine loading. A person of ordinary skill in the art will understand what time frame is meant for administration "before exercise" or "immediately before exercise". Other uses of the creatine carbonate composition include preventing, treating, or curing various conditions that result in decreased physical performance, fatigue, and malaise.

For simplicity, such diseases and conditions will be referenced as "creatine carbonate improvable conditions". Creatine carbonate improvable conditions include, but are not limited to, cerebral creatine deficiency syndromes, sarcopenia, amyotrophic lateral sclerosis (ALS, Lou Gehrig's disease), Huntington disease, osteopenia, age-related cognitive decline, aging skin, chronic kidney disease (CKD), chronic obstructive pulmonary disease (COPD), cognitive function, congestive heart failure (CHF), depression, diabetes, fatigue, fibromyalgia, gyrate atrophy, hereditary motor and sensory neuropathy, HIV/AIDS-related wasting, hyperhomocysteinemia, inflammatory myopathies, juvenile idiopathic arthritis (JIA), McArdle disease, mitochondrial myopathies, multiple sclerosis (MS), muscle breakdown, muscle cramps, muscular dystrophy, neonatal apnea, osteoarthritis, Parkinson disease, peripheral arterial disease (PAD), post-operative recovery, Rett syndrome, rheumatoid arthritis (RA), schizophrenia, spinal cord injury, spinal muscular atrophy, and traumatic brain injury (TBI).

The symptoms and etiology of creatine carbonate-improvable conditions that can be ameliorated by the administration of creatine carbonate and the formulations described herein are described in the "Handbook of Diseases 3rd Edition by Springhouse Corporation", which is fully incorporated by reference herein.

Thus, methods of using creatine carbonate are also described herein. The methods generally comprise orally administering to a subject an effective amount of creatine carbonate to achieve the desired effect. The effective amount can be administered before, during or after physical exercise or work. In some implementations, the effective amount is administered 5 to 120 minutes before physical exercise or work or in some different implementations immediately before. In the case of treating diseases and conditions, the effective amount may be administered once per day, multiple times per day, or continuously through the day via time release, delayed release, or extended release formulations.

The dosage for creatine carbonate ranges from 1 mg to 30,000 mg per day, which can be split into one or more dosages. For example, a daily dose of 1 mg to 30,000 mg creatine carbonate is orally administered in one, two, three, or four administrations. For exercise performance enhancing purposes, the formulation is administered (for example, by ingestion) prior to exercise, for example any time between 3 days prior to exercise and right before exercise. In certain implementations, the formulation is administered one hour before exercise. In other implementations, the formulation is administered during exercise, or any time after exercise to assist with muscle building, lactic acid removal, and recovery. For purposes of treating, preventing or curing a creatine carbonate-improvable condition, the formulation is administered in a pharmaceutically effective amount to treat, as needed, said condition or disease.

Compositions and/or formulations of the present invention may be administered in any form, including one of a capsule, a cachet, a pill, a tablet, a powder, a granule, a pellet, a bead, a particle, a troche, a lozenge, a pastille, a solution, an elixir, a syrup, a tincture, a suspension, an emulsion, a mouthwash, a spray, a drop, an ointment, a cream, a gel, a paste, a transdermal patch, a suppository, a pessary, cream, a gel, a paste, a foam, and combinations thereof for example. Compositions and/or formulations of the present invention may also include an acceptable additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or an acceptable carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof).

Implementations of the creatine carbonate compositions may conveniently be presented in unit dosage form. Unit dosage formulations may be those containing a daily dose or unit, a daily sub-dose, or an appropriate fraction thereof, of the administered components as described herein.

A dosage unit may include creatine carbonate and preferably a dissolution enhancer such as sodium carbonate, potassium carbonate, magnesium carbonate, calcium carbonate, zinc carbonate, copper carbonate and iron carbonate, sodium bicarbonate, potassium bicarbonate, magnesium bicarbonate, calcium bicarbonate, zinc bicarbonate, copper bicarbonate and iron bicarbonate. In addition, a dosage unit may include the creatine carbonate admixed with a pharmaceutically acceptable additive(s), and/or any combination thereof.

The dosage units may be in a form suitable for administration by standard routes. In general, the dosage units may be administered, by non-limiting example, by the topical (including buccal and sublingual), transdermal, oral, rectal, ophthalmic (including intravitreal or intracameral), nasal, vaginal, and/or parenteral (including subcutaneous, intramuscular, intravenous, intradermal, intratracheal, and epidural) routes. In some implementations, the dosage unit include the creatine carbonate in a coated, microencapsulated, or other form that prevent dissolution of creatine carbonate in water or any other solvent in which the creatine carbonate is administered. The dosage unit may also include the creatine carbonate dissolved or in suspension in a suitable liquid, such as, but not limited to, glycerol, water, various oils, and alcohol. Examples include coating creatine carbonate particles by lecithin, carnauba wax, shellac (for enteric release) or a fatty acid such as stearic acid. A dosage unit may also include the creatine carbonate in a time release, delayed release or prolonged release form.

For the exemplary purposes of this disclosure, oral delivery may be a particularly advantageous delivery route for administration to humans and animals of implementations of a pharmaceutical composition, optionally formulated with appropriate pharmaceutically acceptable additives to facilitate administration.

In some implementations, the creatine carbonate composition further comprises additional supplements or ingredients that enhance the effectiveness of creatine carbonate. These supplements or ingredients include, but are not limited to: 1,3-DMAA, 1,3-DMBA, 1,4-Butanediol, 1,4-DMAA, 1-Androsterone, 1-Epiandrosterone, 19-nor-DHEA, 4-Androsterone, 5-decazol, 5-HTP, 5aOHP, 6-Bromo, 7,8-benzoflavone, 7-alphahydroxy-DHEA, 7-beta-hydroxy-DHEA, 7-Keto-DHEA, 7-methoxyflavone, abscess root, abuta, acacia rigidula, acai, acerola, ackee, aconite, activated charcoal, active hexose correlated compound (AHCC), adenosine, adrafinil, adrenal extract, adrue, aegeline, african wild potato, agar, agaricus mushroom, agave, agmatine, agrimony, *Ajuga nipponensis*, alanine, *Albizia julibrissin*, alchemilla, alder buckthorn, aletris, alfalfa, algal oil, algin, alkanna, allspice, aloe, alpha-GPC, alpha-ketoglutarate (AKG), alpha-linolenic acid (ALA), alpha-lipoic acid, alpine ragwort, alpinia, amaranth, ambrette, American adder's tongue, American chestnut, American dogwood, American elder, American *ginseng*, American hellebore, American ivy, American mistletoe, American pawpaw, American spikenard, American white water lily, andarine, andiroba, andrographis, androstenediol, androstenedione, androstenetrione, androsterone, angel's trumpet, *Angelica archangelica*, angostura, anhydrous crystalline maltose, anise, annatto, antineoplastons, antioxidants, apoaequorin, apple, apple cider vinegar, apple polyphenols, apricot, apricot kernel, arabinoxylan, arenaria rubra, arimistane, aristolochia, arnica, arrach, arrowroot, arsenic, artemisia herba-alba, artichoke, arum, asafoetida, asarabacca, *Ascophyllum nodosum*, ascorbigen, ash, ashitaba, ashwagandha, asian water plantain, asparagus, asparagus racemosus, aspartic acid, aspen, astaxanthin, astragalus, atlantic cedar, atractylodes, autumn crocus, avens, avocado, avocado soy unsaponifiables (asu), avocado sugar extract, ayahuasca, babassu, bach flower remedies, *Bacillus coagulans*, bael, baikal skullcap, bajitian, bamboo, banaba, banana, baobab, barley, basil, bay leaf, bayberry, bear's garlic, bee pollen, bee venom, beer, beeswax, beet, belladonna, benfotiamine, benzoin, berberine, bergamot, beta-alanine, beta-carotene, betacryptoxanthin, beta-glucans, beta-hydroxybutyrate (BHB), beta-methylphenethylamine (BMPEA), beta-sitosterol, betaine anhydrous, betaine hydrochloride, betel nut, beth root, betony, *Bifidobacterium animalis* subsp, *lactis, Bifidobacterium bifidum, Bifidobacterium breve, Bifidobacterium longum*, bilberry, biotin, birch, bishop's weed, bismuth, bismuth nitrate, bistort, bitter almond, bitter melon, bitter milkwort, bitter orange, bitter yam, bittersweet nightshade, black alder, black bryony, black cohosh, black currant, black haw, black hellebore, black hoof mushroom, black horehound, black mulberry, black mustard, black nightshade, black pepper, black psyllium, black raspberry, black rice, black root, black seed, black tea, black walnut, blackberry, blackthorn, blessed thistle, blond psyllium, bloodroot, blue cohosh, blue flag, blue-green algae, blueberry, bog bilberry, bog labrador tea, bogbean, bois de rose oil, boldo, boneset, borage, boron, boswellia serrata, bovine cartilage, bovine colostrum, boxwood, branched-chain amino acids (BCAA), breadfruit, brewer's yeast, brickellia, bridelia, broccoli, broccoli sprout, bromelain, brown rice, brussels sprout, bryonia, buchu, buck's-horn plantain, buckhorn plantain, buckwheat, bugle, bugleweed, *Bulbine natalensis*, bulbous buttercup, bupleurum, burdock, burning bush, burr marigold, butcher's broom, butea superba, butterbur, buttercup, butternut, butylated hydroxytoluene (BHT), cabbage, cade, caffeic acid, caffeine, cajeput oil, calabar bean, calabash chalk, calamint, calamus, calanus oil, calcium, calcium D-glucarate, *Calea zacatechichi*, calendula, california poppy, calotropis, calumba, camphor, camu camu, canada balsam, canadian fleabane, canadian hemp, canaigre, cananga oil, cannabichromene (CBC), cannabidiol (CBD), cannabidivarin (CBDV), cannabigerol (CBG), cannabinol (CBN), cannabis, canola oil, canthaxanthin, capers, caprylic acid, capsicum, caralluma, caraway, carbon 60 (C60), cardamom, cardarine, carlina, carnosine, carob, carqueja, carrageenan, carrot, cascara sagrada, cascarilla, casein peptides, casein protein, cashew, cassava, cassia auriculata, cassia cinnamon, cassia nomame, cassie absolute, castor bean, castoreum, cat's claw, cat's foot, catechu, catnip, catuaba, cauliflower, celery centaury, cereus, cesium, cetylated fatty acids (CFAs), ceylon cinnamon, ceylon leadwort, cha de bugre, chaga, chanca piedra, chaparral, chaulmoogra, cheken, chelation therapy products, chenopodium oil, chervil, chia, chickweed, chicory, Chinese cucumber, Chinese mallow, Chinese prickly ash, chirata, chitosan, chive, chlorella, chlorine dioxide, chlorophyll, chlorophyllin, chokeberry, chondroitin sulfate, chromium, chrysanthemum, chrysin, chuchuhuasi, chymotrypsin, cilantro, cinchona, *Cissus quadrangularis, Cistanche deserticola*, citicoline, citric acid, citronella oil, clary sage, clay, *Clematis recta*, clivers, clove, clown's mustard plant, clubmoss, cnidium, cobalt, coca, cocillana, cocoa, coconut, coconut oil, coconut water, cod liver oil, codonopsis, coffee, coffee charcoal, cola nut, coleus, collagen peptides, collagen type I (native), collagen type II (native), collard, colloidal minerals, colloidal silver, colocynth, coltsfoot, columbine, *Combretum micranthum*, comfrey, common stonecrop, condurango, conjugated linoleic acid (CLA), copaiba balsam, copper, coral, cordyceps, coriander, corkwood tree, corn poppy, corn silk, cornflower, Corydalis yanhusuo, costus, cotton, couch grass, cowhage, cowslip, cramp bark, cranberry, creatine, croton seeds, cubebs, cucumber, cudweed, cumin, cursed buttercup, cyanostane, cyclamen, cypress, d-mannose, daffodil, damiana, dandelion, danshen, date palm, *Datura wrightii*, deanol, deer velvet, delta-8-tetrahydrocannabinol (delta-8-THC), delta-9-tetrahydrocannabinol (delta-9-THC), dendrobium, desert parsley, devil's claw, devil's club, dhea, diacylglycerol, diatomaceous earth, diindolylmethane, diiodothyronine, dill, dimethylglycine (DMG), dimethylhexylamine (DMHA), dimethylsulfoxide (DMSO), diosmin, divi-divi, docosahexaenoic acid (DHA), dodder, dolomite, dong quai, douglas fir, dragon fruit, dragon's blood, duckweed, dulse, durabolin, durian, dusty miller, dwarf elder, dwarf pine needle, dyer's broom, dymethazine, eastern hemlock, eastern red cedar, ecdysteroids, echinacea, *Ecklonia cava*, eicosapentaenoic acid (EPA), elderberry, elderflower, elecampane, elemi, eleuthero, ellagic acid, elm bark, emu oil, English adder's tongue, English horsemint, English ivy, English walnut, ephedra, epiandrosterone, epistane, equol, ergot, ergothioneine, eryngo, eucalyptus, *Euphorbia cyparissias, Euphorbia hirta*, European barberry, European buckthorn, European chestnut, European five-finger grass, European mandrake, European mistletoe, *Eurycoma longifolia*, evening primrose, evodia, eyebright, *Fadogia agrestis*, false unicorn, fennel, fenugreek, fermented milk, fermented wheat germ extract, fever bark, feverfew, ficin, field scabious, fig, figwort, fir, fireweed, fish oil, flaxseed, flaxseed oil, fluoride, fly agaric mushroom, fo-ti, folic acid, fool's parsley, forget-me-not, forsythia, foxglove, frankincense, fringetree, frostwort, fructo-oligosaccharides (FOS), *Fucus Vesiculosus*, fulvic acid, fumitory, galacto-oligosaccharides (GOS), galbanum, *Galphimia glauca*, gamboge, gamma butyrolactone (GBL), gamma-aminobutyric acid (GABA), gamma-hydroxybutyrate (GHB), gamma-linolenic acid (GLA), gamma-oryzanol, garcinia, garden cress, gardenia, garlic, gelatin, gelsemium, genistein combined polysaccharide, gentian, German chamomile, German ipecac, German sarsaparilla, germander, germanium, ginger, ginkgo, globe flower, globemallow, glossy privet, glucomannan, glucosamine, glucuronolactone, glutaurine, glutathione, glycerol, glycine, glycolic acid, glycomacropeptide, glyconutrients, goa powder, goat's rue, goji, golden ragwort, goldenrod, goldenseal, goldthread, gossypol, gotu kola, goutweed, grains of paradise, grape, grapefruit, gravel root, graviola, great plantain, greater burnet, greater celandine, greek sage, green coffee, green tea, *Griffonia simplicifolia*, ground ivy, ground pine, groundsel, guaiac wood, guar gum, guarana, guarumo, guava, guggul, gum arabic, gumweed, gymnema, halodrol-50, haronga, hartstongue, Hawaiian baby woodrose, hawthorn, hazelnut, heart's ease, heather, hedge mustard, hedge-hyssop, hemlock, hemlock water dropwort, hemp, hemp agrimony, hempnettle, henbane, henna, herb Paris, herb Robert, Hercules club, hesperidin, hexadrone, hexylamine, hibiscus sabdariffa, higenamine, histidine, holly, hollyhock, holy basil, homotaurine, honey, honeysuckle, hoodia, hops, hordenine, horny goat weed, horse chestnut, horsemint, horseradish, horsetail, hound's tongue, houseleek, hu zhang, humic acid, huperzine A, hyacinth bean, hyaluronic acid, hydrangea, hydrazine sulfate, hydroxymethylbutyrate (HMB), hyperimmune egg, hyssop, iboga, Iceland moss, idebenone, ignatius bean, immortelle, Indian cassia, Indian gooseberry, Indian long pepper, Indian snakeroot, indigo pulchra, indium, indole-3-carbinol, inosine, inositol, inositol nicotinate, inulin, iodine, ip-6, ipecac, iporuru, ipriflavone, iron, *Irvingia gabonensis*, isatis, isopropylnorsynephrine, ivy gourd, jaborandi, jackfruit, jalap, Jamaican dogwood, jambolan, Japanese apricot, Japanese mint, Japanese persimmon, jasmine, java tea, Javanese turmeric, jequirity, jewelweed, jiaogulan, jimson weed, job's tears, jojoba, juniper, Justicia pectoralis, K2/spice, kale, kamala, kaolin, karaya gum, kava, kefir, ketogenic diet, khat, khella, kinetin, kiwi, knotweed, kohlrabi, kombucha, Korean pine, kousso, kratom, krill oil, kudzu, L-arginine, L-citrulline, L-cysteine, L-ornithine-L-aspartate, labdanum, laburnum, lactase, lactic acid, *Lacticaseibacillus casei, Lacticaseibacillus paracasei, Lacticaseibacillus rhamnosus, Lactiplantibacillus pentosus, Lactiplantibacillus plantarum, Lactobacillus acidophilus, Lactobacillus crispatus, Lactobacillus delbrueckii, Lactobacillus gasseri, Lactobacillus helveticus, Lactobacillus jensenii, Lactobacillus johnsonii*, lactoferrin, lady's bedstraw, laminaria, larch arabinogalactan, larch turpentine, lathyrus, Latilactobacillus sakei, laurelwood, lauric acid, lavender, lavender cotton, laxogenin, lemon, lemon balm, lemon eucalyptus, lemon verbena, lemongrass, lentinan, lesser celandine, levant berry, Levilactobacillus brevis, licorice, Ligandrol, *Ligilactobacillus salivarius*, lily-of-the-valley, lime, limonene, *Limosilactobacillus fermentum, Limosilactobacillus reuteri*, linden, lingonberry, lion's mane mushroom, lipase, lithium, liver extract, liverwort, lobelia, logwood, Lorenzo's oil, lotus, lousewort, lovage, luffa, lunasin, lungmoss, lungwort, lupin, lutein, lychee, lycopene, lysine, M1-4ADD, maca, macadamia nut, mace, Madagascar periwinkle, madder, magnesium, magnolia, maidenhair fern, maitake mushroom, malabar nut, male fern, malic acid, mallow, manaca, Manchurian thorn, manganese, mangosteen, manna, maqui, maral root, maritime pine, marjoram, marsh blazing star, marsh labrador tea, marsh marigold, marshmallow, masterwort, mastic, meadowsweet, medium chain triglycerides (MCTs), melanotan, melatonin, mentabolan, mercury herb, mesoglycan, methasterone, methionine, methoxydienone, methoxylated flavones, methyldiazinol, methylstenbolone, methylsulfonylmethane (MSM), methylsynephrine, mezereon, milk thistle, miracle fruit, molybdenum, moneywort, monolaurin, Monterey pine, moringa, Mormon tea, motherwort, mountain ash, mountain flax, mountain laurel, mouse-ear hawkweed, mugwort, muira puama, mullein, musk, myrcia, myrrh, myrtle, N, N-DMPEA, N-acetyl cysteine (NAC), N-methyltyramine, nasturtium, nattokinase, neem, nerve root, new jersey tea, New Zealand green-lipped mussel, niacinamide, niauli oil, nickel, nicotinamide riboside, nikko maple, noni, northern prickly ash, Norway spruce, nutmeg, nux vomica, oak moss, oats, octacosanol, octopamine, *oleander*, oleic acid, olive, olive oil, omega-6 fatty acids, onion, oolong tea, orchic extract, oregano, Oregon grape, oriental arborvitae, ornamental marigold, ornithine, ornithine ketoglutarate (OKG), orris, oscillococcinum, osha, ostarine, ostrich fern, oswego tea, ox-eye daisy, padang cassia, pagoda tree, palm oil, palmitoylethanolamide (PEA), *Panax Ginseng, Panax Notoginseng*, pancreatic enzyme products, pangamic acid, pantethine, pao pereira, papain, papaya, para-aminobenzoic acid (PABA), pareira, parsley, parsley piert, parsnip, partridgeberry, passion flower, pata de vaca, patchouli oil, Pau D'Arco, pea protein, peanut oil, pear, pectin, pedunculate oak, pellitory, pellitory-of-the-wall, pennyroyal, peony, peppermint, perilla, perillyl alcohol, periwinkle, peru balsam, peyote, *Phaseolus vulgaris*, pheasant's eye, phellodendron, phenethylamine (PEA), phenibut, phenpromethamine, phlorizin, phosphate salts, phosphatidylcholine, phosphatidylserine, phytase, picamilon, picrorhiza, pimpinella, *Pinellia ternata*, pink root, pipsissewa, piracetam, pitcher plant, plant sterols, pleurisy root, plum, *podophyllum*, poinsettia, poison ivy, pokeweed, polarity therapy, policosanol, polydextrose, *Polypodium leucotomos*, pomegranate, poplar, poppy seed, poria mushroom, potassium, potato, potentilla, pregnenolone, premorse, prickly pear cactus, procaine, progesterone, proline, propolis, proteolytic enzymes (proteases), psilocybin, pu-erh tea, *pulsatilla*, pumpkin, purple loosestrife, purple nut sedge, pygeum, pyrethrum, pyruvate, quassia, quebracho blanco, queen's delight, quercetin, quillaia, quince, quinoa, *Rabdosia rubescens*, radish, raspberry ketone, *Rauvolfia vomitoria*, rauwolscine, red clover, red maple, red raspberry, red sandalwood, red soapwort, red yeast rice, red-spur valerian, reed herb, rehmannia, reishi mushroom, resveratrol, rhatany, rhodiola, rhubarb, riboflavin, ribose, rice bran, rice bran arabinoxylan compound, rice (protein, RNA, or DNA), rock rose, roman chamomile, rooibos, rose geranium oil, rose hip, rosemary, royal jelly, rue, rupturewort, rusty-leaved rhododendron, rutin, rye grass, S-23, *Saccharomyces boulardii*, safed musli, safflower, saffron, sage, saigon cinnamon, salacia, salatrim, salep, *Salvia divinorum*, samphire, sandy everlasting, sangre de grado, sanicle, sarsaparilla, sassafras, savin tops, saw palmetto, scarlet pimpernel, sceletium, schisandra, schizonepeta, scopolia, scotch broom, scotch thistle, scurvy grass, sea buckthorn, sea moss, secretin, *Securinega suffruticosa*, selenium, self-heal, senega, senna, serine, serrapeptase, sesame, sessile oak, shark cartilage, shark liver oil, shea butter, shellac, shepherd's purse, shiitake mushroom, Siberian cocklebur, *Sida cordifolia*, silicon, simaruba, sitostanol, skullcap, skunk cabbage, slippery elm, smartweed, smooth alder, snake skin, sodium, sodium bicarbonate, sodium tetrachloroaurate, Solomon's seal, sorghum, sorrel, soy, soybean oil, Spanish broom, Spanish origanum oil, spearmint, spinach, spiny restharrow, spleen extract, spotted geranium, squalamine, squill, St. John's wort, star anise, star of bethlehem, stavesacre, stenabolic, *Stereospermum*, stevia, stinging nettle, stone root, storax, strawberry, *Streptococcus thermophilus*, strontium, strophanthus, succinate, sulbutiamine, sulforaphane, sulfur, suma, sumbul, summer savory, sundew, sunflower oil, superoxide Dismutase (SOD), swallowroot, swamp milkweed, sweet almond, sweet Annie, sweet cherry, sweet cicely, sweet clover, sweet gale, sweet orange, sweet sumac, sweet vernal grass, sweet violet, sweet woodruff, Syrian rue, tamarind, *Tamarix dioica*, tangerine, tannic acid, tansy, tansy ragwort, tapioca, tarragon, tart cherry, tartaric acid, tea tree oil, teazle, terminalia, testolone, tetrahydrocannabivarin (THCV), theacrine, theaflavin, threonine, thuja, thunder god vine, thyme, thymus extract, thyroid extract, tianeptine, timothy grass, tin, *Tinospora cordifolia*, tiratricol, tocotrienols, tolu balsam, tomato, tonka bean, toothed clubmoss, tormentil, tragacanth, trailing arbutus, transfer factor, traveler's joy, tree of heaven, tree tobacco, tree turmeric, trendione, tribulus, *Trichopus zeylanicus*, tronadora, trypsin, tung seed, turkey corn, turkey tail mushroom, turmeric, turpentine oil, turtlehead, tylophora, tyramine, umckaloabo, usnea, uva ursi, uzara, valerian, vanadium, vanilla, verbena, veronica, vetiver, Vietnamese coriander, vinpocetine, vitamin A, vitamin B1, vitamin B2, vitamin B6 (or a salt, ester, or amide suitable for human ingestion thereof), vitamin B8 (or a salt, ester, or amide suitable for human ingestion thereof), vitamin B9 (or a salt, ester, or amide suitable for human ingestion thereof), vitamin B12 (or a salt, ester, or amide suitable for human ingestion thereof), vitamin C, vitamin D, vitamin E, vitamin K, vitamin O, wafer ash, wahoo, wallflower, wasabi, water avens, water dock, water hemlock, watercress, wheat bran, wheatgrass, whey protein, white dead nettle flower, white hellebore, white horehound, white lily, white mulberry, white mustard, white oak, white pepper, white sandalwood, wild carrot, wild cherry, wild daisy, wild indigo, wild lettuce, wild mint, wild thyme, wild yam, willard water, willow bark, wine, winter cherry, winter savory, wintergreen, witch hazel, wood anemone, wood sage, wood sorrel, wormseed, wormwood, xanthan gum, xanthoparmelia, xylitol, yarrow, yellow dock, yellow loosestrife, yellow toadflax, yerba mansa, yerba mate, yerba santa, yew, yin chen, ylang ylang oil, yogurt, yohimbe, yucca, zeaxanthin, zedoary, zinc, zizyphus, L-carnitine (or a salt, ester, or amide suitable for human ingestion thereof), acetyl-L-carnitine (or a salt, ester, or amide suitable for human ingestion thereof), propionyl-L-carnitine (or a salt, ester, or amide suitable for human ingestion thereof), aniracetam, piracetam, phenylpiracetam, Bacopa monnieri, cannabidiol (CBD), *Celastris paniculatus*, centrophenoxine, *Clitoria ternatea*, coluracetam, *Convolvulus pluricaulis*, ubiquinone (for example, Coenzyme Q10), creatine (or a salt, ester, or amide suitable for human ingestion thereof), choline (or a salt, ester, or amide suitable for human ingestion thereof), dimethylethanolamine (DMAE), forskolin, *Ginkgo biloba*, guarana, kanna, kava kava, L-glutamine (or a salt, ester, or amide suitable for human ingestion thereof), L-phenylalanine (or a salt, ester, or amide suitable for human ingestion thereof), L-theanine (or a salt, ester, or amide suitable for human ingestion thereof), L-tryptophan (or a salt, ester, or amide suitable for human ingestion thereof), lecithin (or a salt, ester, or amide suitable for human ingestion thereof), lemon balm, lion's mane mushroom, magnolia, medium chain triglycerides, reduced nicotinamide adenine dinucleotide (NADH), nefiracetam, nicotine, arecoline, noopept, oatstraw, oxiracetam, passion flower, phenibut, phosphatidylcholine, phosphatidylserine, picamilon, pine bark extract, pramiracetam, pyrroloquinoline quinone (PQQ), pterostilbene, resveratrol, rosemary, *Rhodiola rosea*, S-adenosyl methionine (SAMe), schizandrol-A, St. John's wort, sulbutiamine, taurine (or a salt, ester, or amide suitable for human ingestion thereof), L-tyrosine (or a salt, ester, or amide suitable for human ingestion thereof), N-acetyl-L-tyrosine (or a salt, ester, or amide suitable for human ingestion thereof), uridine, valerian, vinpocetine, thiamine (or a salt, ester, or amide a salt, ester, or amide suitable for human ingestion thereof), niacin (or a salt, ester, or amide suitable for human ingestion thereof), pantothenic acid (or a salt, ester, or amide suitable for human ingestion thereof), and yerba mate.

It should be appreciated that any of the components of particular implementations of creatine carbonate (sodium creatine carbonate or other creatine carbonate) and compositions may be used as supplied commercially, or may be preprocessed by, by non-limiting example, any of the methods and techniques of agglomeration, air suspension chilling, air suspension drying, balling, coacervation, comminution, compression, pelletization, cryopelletization, extrusion, granulation, homogenization, inclusion compoundation, lyophilization, melting, mixed, molding, pan coating, solvent dehydration, sonication, spheronization, spray chilling, spray congealing, spray drying, or other processes known in the art depending in part on the dosage form desired. The various components may also be pre-coated or encapsulated as known in the art. It will also be clear to one of ordinary skill in the art that appropriate additives may also be introduced to the composition or during the processes to facilitate the preparation of the dosage forms, depending on the need of the individual process.

Those of ordinary skill in the art will be able to readily select manufacturing equipment and pharmaceutically acceptable additives or inert ingredients to manufacture implementations of the creatine carbonate. For the exemplary purposes of this disclosure, some examples of pharmaceutically acceptable additives or inert ingredients and manufacturing processes are included herein, particularly those that relate to manufacture of implementations of the creatine carbonate in tablet form or powder form.

Notwithstanding the specific examples given, it will be understood that those of ordinary skill in the art will readily appreciate how to manufacture implementations of the creatine carbonate composition according to the other methods of administration and delivery disclosed in this document.

Particular implementations of the composition include a lubricant. Lubricants are any anti-sticking agents, glidants, flow promoters, and the like materials that perform a number of functions in tablet manufacture, for example, such as improving the rate of flow of the tablet granulation, preventing adhesion of the tablet material to the surface of the dies and punches, reducing interparticle friction, and facilitating the ejection of the tablets from the die cavity. Lubricants may comprise, for example, magnesium stearate, calcium stearate, talc, and colloidal silica.

Particular implementations of the composition include a binder. Binders are any agents used to impart cohesive qualities to powdered material through particle-particle bonding. Binders may include, for example, matrix binders (e.g., dry starch, dry sugars), film binders (e.g., celluloses, bentonite, sucrose), and chemical binders (e.g., polymeric cellulose derivatives, such as methyl cellulose, carboxy methyl cellulose, and hydroxy propyl cellulose); and other sugar, gelatin, non-cellulosic binders and the like.

Disintegrators may be used in particular implementations of the composition to facilitate the breakup or disintegration of tablets after administration. Disintegrators may include, for example, starch, starch derivatives, clays (e.g., bentonite), algins, gums (e.g., guar gum), cellulose, cellulose derivatives (e.g., methyl cellulose, carboxymethyl cellulose), croscarmellose sodium, croscarmellose cellulose, and other organic and inorganic materials.

Implementations of the composition may also include diluents, or any inert substances added to increase the bulk of the creatine carbonate to make a tablet a practical size for compression. Diluents may include, for example, calcium phosphate, calcium sulfate, lactose, mannitol, magnesium stearate, potassium chloride, and citric acid, among other organic and inorganic materials.

Buffering agents may be included in compositions as well and may be any one of an acid and a base, where the acid is, for example, propionic acid, p-toluenesulfonic acid, salicylic acid, stearic acid, succinic acid, tannic acid, tartaric acid, thioglycolic acid, or toluenesulfonic acid, and the base is, for example, ammonium hydroxide, potassium hydroxide, sodium carbonate, potassium carbonate, sodium hydroxide, sodium hydrogen carbonate, aluminum hydroxide, calcium carbonate, and other organic and inorganic chemicals.

Creatine carbonate may also be administered through use of amphipathic lipid delivery systems (such as liposomes and unilamellar vesicles), caplet systems, oral liquid systems, parenteral and/or intravenous systems, topical systems (creams, gels, transdermal patches, etc.), intranasal systems, rectal or vaginal systems, and many other delivery methods and/or systems known to those of ordinary skill in the art. Those of ordinary skill in the art will readily be able to select additional pharmaceutically acceptable additives to enable delivery of implementations of a pharmaceutical composition from the disclosure in this document.

With respect to delivery of particular uses of creatine carbonate, for the exemplary purposes of this disclosure, tablets may be utilized. Tablets are any solid pharmaceutical dosage form containing a pharmaceutically acceptable active agent or agents to be administered with or without suitable pharmaceutically acceptable additives and prepared either by compression or molding methods well known in the art. Tablets have been in widespread use and remain popular as a dosage form because of the advantages afforded both to the manufacturer (e.g., simplicity and economy of preparation, stability, and convenience in packaging, shipping, and dispensing) and the patient (e.g., accuracy of dosage, compactness, portability, blandness of taste, and ease of administration). Although tablets are most frequently discoid in shape, they may also be, for example, round, oval, oblong, cylindrical, rectangular, or triangular. The tablets may be optionally scored so that they may be separated into different dosages. They may differ greatly in size and weight depending on the amount of the pharmaceutically acceptable active agent or agents present and the intended route of administration. They are divided into two general classes: compressed tablets and molded tablets.

Furthermore, creatine carbonate may be combined in various ways with an acid to produce an effervescent composition. In some aspects, the creatine carbonate and the acid are combined in a tablet to produce an "effervescent tablet". Effervescent tablets are designed to release carbon dioxide upon contact with water, promoting their disintegration. A common drawback of conventional effervescent tablets is that they are commonly formulated by combining sodium bicarbonate with an acid. Thus, conventional effervescent compositions increase sodium intake, which is often a health drawback. On the other hand, creatine carbonate can be made into effervescent tablets or powders and various single dosage forms such as stick packs without the need of adding sodium bicarbonate, sodium carbonate, or any other bicarbonate salt or carbonate salt. Thus, an effervescent composition for creatine supplementation using creatine carbonate minimizes negative health effect concerns related to increased sodium intake.

Tablets and other orally discrete dosage forms, such as capsules, cachets, pills, granules, pellets, beads, and particles, for example, may optionally be coated with one or more enteric coatings, seal coatings, film coatings, barrier coatings, compress coatings, fast disintegrating coatings, or enzyme degradable coatings for example. Multiple coatings may be applied for desired performance. Further, dosage forms may be designed for, by non-limiting example, immediate release, pulsatile release, controlled release, extended release, delayed release, targeted release, synchronized release, or targeted delayed release. For release/absorption control, carriers may be made of various component types and levels or thicknesses of coats. Such diverse carriers may be blended in a dosage form to achieve a desired performance. In addition, the dosage form release profile may be affected by a polymeric matrix composition, a coated matrix composition, a multiparticulate composition, a coated multiparticulate composition, an ion-exchange resin-based composition, an osmosis-based composition, or a biodegradable polymeric composition.

The contents of all references, patents, and published patent applications cited throughout this specification, if any, are incorporated herein by reference in their entirety for all purposes.

EXAMPLES

The present disclosure is further illustrated by the following examples that should not be construed as limiting.

Example 1

Figure 2:
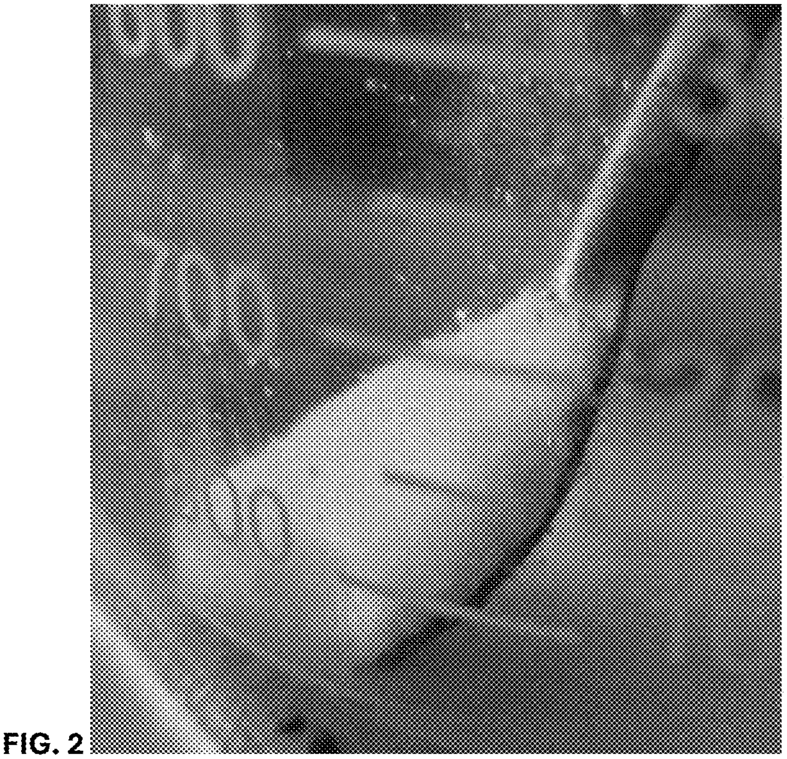
FIG. 2 is a photograph depicting the production of gases from adding the precipitate produced from combining the creatine salt and the carbonate salt to an acidified citric acid solution.
Figure 3:
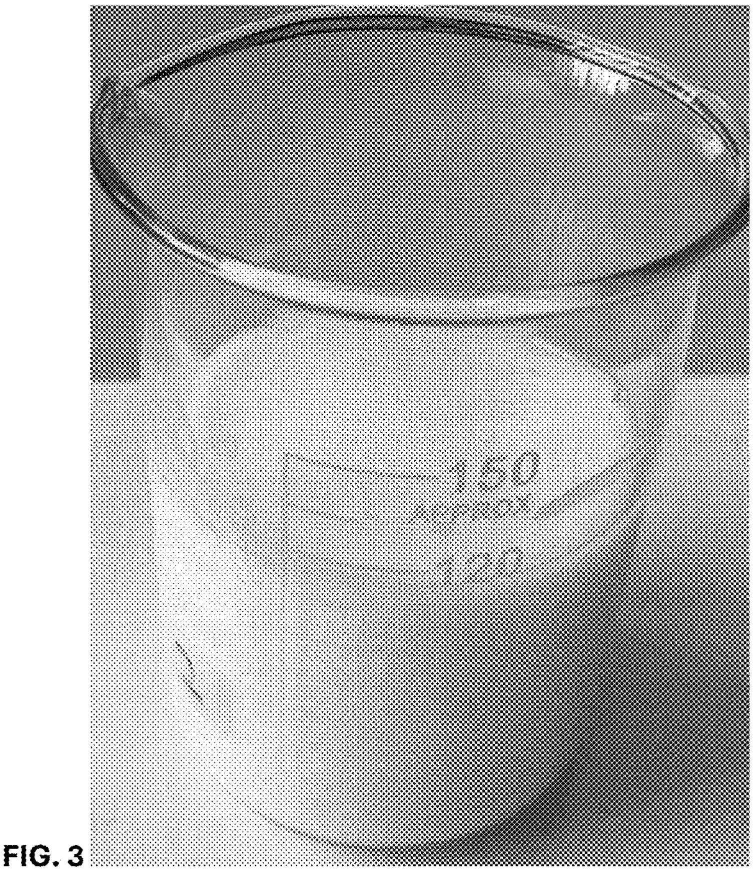
FIG. 3 is a photograph depicting the cloudy solution produced from passing the gas produced from FIG. 2 through a calcium hydroxide solution.

Creatine carbonate was synthesized by first dissolving 2 moles (about 192 g) of ammonium carbonate in 1000 ml of cold water (0-1° C.). The solution of ammonium carbonate was slowly combined with 1 mole (about 167.59 g) of creatine hydrochloride. The solution was continuously stirred during the addition of creatine hydrochloride. The resulting precipitate was collected by filtration and air dried. The presence of carbonate in the precipitate was confirmed by adding the precipitate into an acidified citric acid solution and observing the produced gas (FIG. 2). When the resulting gas was passed in a lime water (calcium hydroxide solution), it turned the solution cloudy (FIG. 3), per the reaction $CO_2+Ca(OH)_2 \rightarrow CaCO_3+H_2O$.

Example 2

A male subject, 42 years old, trained, was administered 5 g creatine carbonate and monitored for any gastrointestinal tract symptoms. He did not experience any unwanted gastrointestinal tract issues except a little belching. In contrast, the subject would develop a bloated stomach with creatine supplements currently on the market.

For example, when the subject ingested 20 g creatine monohydrate once per day with 1000 ml of water for 5 consecutive days, gastrointestinal disturbances, such as diarrhea and stomach bloating, occurred. At the end on day 5, the subject was able to perform 8 knee extensions at 80% maximum weight (200 lbs.). This was 2 more than his usual 6 extensions with this weight (control). So, creatine supplementation with creatine monohydrate improved the subject's physical performance though with gastrointestinal side effects.

After a washout period of 14 days, where the subject ingested no creatine supplements, he began a second period of creatine supplementation with 20 g creatine carbonate, also taken once per day with 1000 ml water. Besides light belching, no other gastrointestinal side effects were noted. At the end of the creatine supplementation with creatine carbonate, the subject again evaluated the effect of creatine supplementation with knee extension exercises at 80% maximum weight (200 lbs.). He performed 10 extensions, which was better than either the control or after 5 days of creatine monohydrate supplementation. Thus, creatine carbonate appears to be a safer, more tolerable, and more effective form of creatine supplementation than creatine monohydrate, despite 20 g creatine carbonate providing slightly less creatine than 20 g creatine monohydrate (about 81.4% creatine in creatine carbonate versus about 87.9% creatine in creatine monohydrate).

Example 3

A 43-year-old recreationally active male used the treadmill at 5 miles per hour for 10 minutes and measured his lactate levels using a Heartscare C1 lactate monitoring system. His blood lactate measured at 8.1 mmol/L. After a two-day washout period, he repeated the same treadmill exercise 60 minutes after ingesting 10 g creatine carbonate. His blood lactate measured at 7.1 mmol/L. Thus, even without creatine loading, creatine carbonate can reduce lactate production from exercise, as measured by blood lactate level.

The invention claimed is:

1. A compound of the formula:

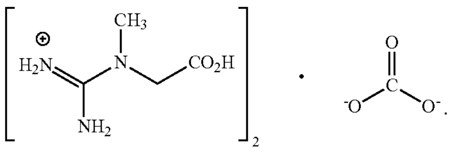

2. A dietary supplement comprising a therapeutically effective dose of creatine carbonate, wherein the creatine carbonate is of the formula:

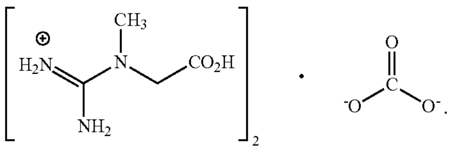

3. The dietary supplement of claim 2, wherein the amount of creatine carbonate in a dosage is about 1 mg to about 30,000 mg.

4. The dietary supplement of claim 2, wherein the dietary supplement is in the form of a capsule, a cachet, a pill, a tablet, a powder, a granule, a pellet, a bead, a lozenge, a solution, a suspension, an emulsion, a transdermal patch, a suppository, a pessary, a cream, a gel, a paste, a foam, or combinations thereof.

5. The dietary supplement of claim 2, further comprising one or more of a solubilizer, an anticoagulant, an antifoaming agent, an antioxidant, a coloring agent, a coolant, a cryoprotectant, a flavoring agent, a plasticizer, a preservative, a sweetener, a thickener, and an acceptable carrier.

6. The dietary supplement of claim 5, wherein the acceptable carrier comprises an excipient.

7. A pharmaceutical composition comprising a therapeutically effective dose of creatine carbonate, wherein the creatine carbonate is of the structure:

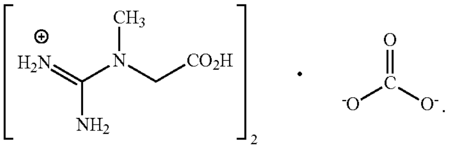

8. The pharmaceutical composition of claim 7, where in the daily dosage of creatine carbonate is 1 to 30,000 mg of creatine in one or multiple doses.

9. The pharmaceutical composition of claim 7, wherein the dose is in the form of a capsule, a cachet, a pill, a tablet, a powder, a granule, a pellet, a bead, a lozenge, a solution, a suspension, an emulsion, a transdermal patch, a suppository, a pessary, a cream, a gel, a paste, a foam, or combinations thereof.

10. The pharmaceutical composition of claim 7, further comprising one or more of a solubilizer, an anticoagulant, an antifoaming agent, an antioxidant, a coloring agent, a coolant, a cryoprotectant, a flavoring agent, a plasticizer, a preservative, a sweetener, a thickener, and an acceptable carrier.

11. The pharmaceutical composition of claim 10, wherein the acceptable carrier comprises an excipient.

12. A method of synthesizing creatine carbonate of the structure:

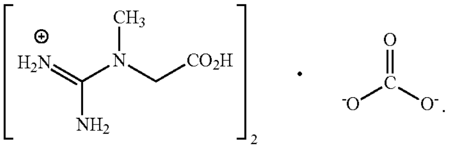

comprising reacting a creatine salt with a carbonate salt.

13. The method of claim 12, wherein the creatine salt is creatine hydrochloride.

14. The method of claim 12, wherein the carbonate salt is ammonium carbonate.

15. The method of claim 12, wherein the creatine salt is creatine hydrochloride and the carbonate salt is ammonium carbonate.

16. The method of claim 15, wherein the method comprises: dissolving ammonium carbonate in water to produce a solution; and adding creatine hydrochloride to the solution thereby producing a precipitate, wherein the molar ratio of ammonium carbonate to creatine hydrochloride is about 2:1 and the precipitate is creatine carbonate.

17. The method of claim 16, further comprising collecting the precipitate by filtration.

18. The method of claim 17, further comprising drying the precipitate.

19. A method comprising administering creatine carbonate to a subject at a daily dosage of 1 to 30,000 mg to treat a creatine carbonate improvable condition selected from one or more of sarcopenia, muscle breakdown and muscle cramps, wherein the subject is administered the creatine carbonate in one or more doses, and wherein the creatine carbonate is of the structure:

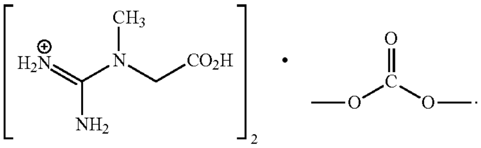

20. The method of claim 19, wherein the subject is administered the daily dosage in one dose.

21. The method of claim 19, wherein the subject is administered the daily dosage in two to four doses.

22. The method of claim 19, wherein the creatine carbonate is administered in a dosage form selected from the group consisting of: a capsule, a cachet, a pill, a tablet, a powder, a granule, a pellet, a bead, a lozenge, a solution, a suspension, an emulsion, a transdermal patch, a suppository, a pessary, a cream, a gel, a paste, a foam, and combinations thereof.

23. The method of claim 19, wherein the creatine carbonate is administered in a composition further comprising one or more of a solubilizer, an anticoagulant, an antifoaming agent, an antioxidant, a coloring agent, a coolant, a cryoprotectant, a flavoring agent, a plasticizer, a preservative, a sweetener, a thickener, and an acceptable carrier.

24. The method of claim 23, wherein the acceptable carrier comprises an excipient.

25. The method of claim 23, wherein the composition is a dietary supplement.

26. The method of claim 23, wherein the composition is a pharmaceutical composition.

27. The method of claim 19, wherein the subject is administered creatine carbonate topically, transdermally, orally, rectally, ophthalmically, nasally, vaginally, or parenterally.

28. The method of claim 19, wherein the subject is administered creatine carbonate orally.

29. The method of claim 28, wherein subject is administered the creatine carbonate in an effervescent formulation comprising the creatine carbonate and an acid.

30. The method of claim 29, wherein the effervescent formulation further comprises a second carbonate salt or bicarbonate salt, wherein the second carbonate salt or bicarbonate salt is not the creatine carbonate.

31. A method of decreasing lactate production from physical activity, the method comprising administering to a subject prior to the subject performing the physical activity an effective amount of creatine carbonate, wherein the creatine carbonate is of the structure:

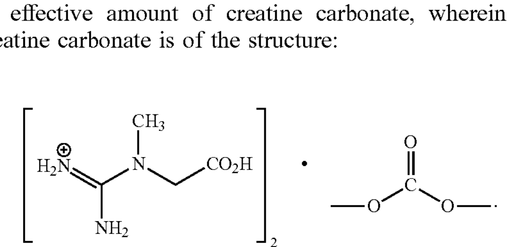

32. The method of claim 31, wherein the subject is orally administered the creatine carbonate 5 to 120 minutes before the subject performs the physical activity.

33. An effervescent formulation comprising: creatine carbonate, wherein the creatine carbonate is of the structure:

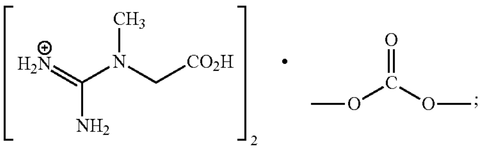

; and an acid.

34. The effervescent formulation of claim 33, wherein the effervescent formulation does not comprise any other carbonate salt or bicarbonate salt other than the creatine carbonate.

35. The dietary supplement of claim 4, wherein the lozenge comprises one or more of a troche and a pastille, and wherein the solution comprises one or more of an elixir, a mouthwash, a spray, a syrup, a drop, and a tincture.

36. The dietary supplement of claim 6, wherein the excipient comprises one or more of a lubricant, a binder, a disintegrator, a diluent, an extender, a solvent, a suspending agent, a dissolution aid, an isotonic agent, a buffering agent, and a soothing agent.

37. The pharmaceutical composition of claim 9, wherein the lozenge comprises one or more of a troche and a pastille, and wherein the solution comprises one or more of an elixir, a mouthwash, a spray, a syrup, a drop, and a tincture.

38. The pharmaceutical composition of claim 11, wherein the excipient comprises one or more of a lubricant, a binder, a disintegrator, a diluent, an extender, a solvent, a suspending agent, a dissolution aid, an isotonic agent, a buffering agent, and a soothing agent.

39. The method of claim 24, wherein the excipient comprises one or more of a lubricant, a binder, a disintegrator, a diluent, an extender, a solvent, a suspending agent, a dissolution aid, an isotonic agent, a buffering agent, and a soothing agent.

* * * * *